United States Patent

Uno et al.

[11] Patent Number: 5,801,270
[45] Date of Patent: Sep. 1, 1998

[54] AMINE DERIVATIVE AND DETERGENT COMPOSITION CONTAINING THE SAME

[75] Inventors: Mitsuru Uno; Tomohito Kitsuki, both of Wakayama; Katsumi Kita, Izumisano; Yoshiaki Fujikura, Utsunomiya; Akiko Okutsu, Sakai, all of Japan

[73] Assignee: Kao Corporation, Tokyo, Japan

[21] Appl. No.: 646,338

[22] PCT Filed: Nov. 14, 1994

[86] PCT No.: PCT/JP94/01923

§ 371 Date: Jun. 13, 1996

§ 102(e) Date: Jun. 13, 1996

[87] PCT Pub. No.: WO95/16664

PCT Pub. Date: Jun. 22, 1995

[30] Foreign Application Priority Data

| Dec. 15, 1993 | [JP] | Japan | 5-314987 |
| Dec. 15, 1993 | [JP] | Japan | 5-314988 |
| Feb. 23, 1994 | [JP] | Japan | 6-025108 |
| Jul. 8, 1994 | [JP] | Japan | 6-157556 |

[51] Int. Cl.$^6$ ............. C07C 229/00; C11D 1/04; C11D 1/46
[52] U.S. Cl. ............. 560/169; 510/126; 510/489; 510/490; 510/492; 510/494; 510/499; 510/501; 510/502; 510/503; 560/170; 562/102; 562/103; 562/582
[58] Field of Search ............. 510/489, 490, 510/499, 492, 503, 501, 502, 126, 494; 564/159; 560/170, 169; 562/103, 102, 582

[56] References Cited

U.S. PATENT DOCUMENTS 5,099,065  3/1992  Kubo et al. ............. 562/564
5,318,727  6/1994  Ohtawa et al. ............. 252/547

FOREIGN PATENT DOCUMENTS

| 4108603 | 9/1992 | Germany. |
| 0551352 | 3/1993 | Japan. |
| 2241234 | 8/1991 | United Kingdom. |

*Primary Examiner*—Shailendra Kumar
*Attorney, Agent, or Firm*—Oblon, Spivak, McClelland, Maier & Neustadt, P.C.

[57] ABSTRACT

The present invention relates to an amine derivative represented by the following general formula (1):

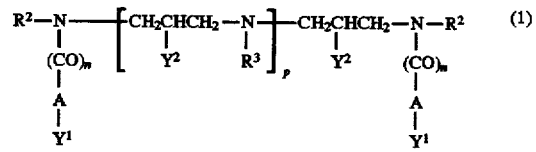

wherein $R^2$ and $R^3$ mean individually an alkyl or alkenyl group which may have —OH and has 1–24 carbon atoms, A denotes an alkylene or alkenylene group which may have at least one —OH, —COOH or —SO$_3$H and has 1–6 carbon atoms, $Y^1$ is —COOH, —SO$_3$H or —OSO$_3$H, $Y^2$ means —OH, —OSO$_3$H or —OCO—A—COOH, n stands for a number of 0 or 1, and p is an integer of 1–8, or a salt or quaternized product thereof, and a detergent composition containing such a compound. This compound is low in irritativeness to the skin and hair and excellent in foamability, and can give a pleasant feeling to the user's skin and the like.

6 Claims, 1 Drawing Sheet

AMINE DERIVATIVE AND DETERGENT COMPOSITION CONTAINING THE SAME

This application is a 371 of PCT/JP94/01923, filed Nov. 14, 1994.

TECHNICAL FIELD

The present invention relates to an amine derivative, or a salt or quaternized product thereof, which is useful as a base for hair and skin cosmetic compositions, a detergent, an emulsifying agent, a conditioning agent, or the like; an intermediate useful for the preparation thereof; and detergent compositions containing such a derivative.

BACKGROUND ART

Surfactants such as alkylsulfates, polyoxyethylene alkylsulfates and alkylbenzenesulfonates have heretofore been used as detergents. However, many of these surfactants involve a problem that they irritate the skin to a somewhat strong extent upon their use. For this reason, surfactants low in skin irritation, such as alkylphosphates and salts of acylated amino acids, have come to be used as bases for hair and skin cosmetic compositions, emulsifying agents or detergents for the skin and the like. With the diversification of demand and inclination to high-quality goods of consumers, there have recently been demand for development of compounds which have good foamability and such effects that a pleasant feeling can be given to the user's skin and the like, in addition to low irritativeness to the skin and the like. However, no compound fully satisfying these requirements has been yet developed.

Accordingly, it is an object of the present invention to provide a compound which can solve the above problems, is low in irritativeness to the skin and the like and excellent in foamability, can give a pleasant feeling to the user's skin and the like, and is useful as a base for hair and skin cosmetic compositions, a detergent, an emulsifying agent, a conditioning agent, or the like.

DISCLOSURE OF THE INVENTION

In view of the foregoing circumstances, the present inventors have carried out an extensive investigation. As a result, it has been found that a novel compound represented by the general formula (1), which will be described subsequently, is low in irritativeness to the skin and the like, gives a pleasant feeling to the user's skin and the like, and has excellent foamability, and that the incorporation of this compound permits the provision of a detergent excellent in detergency and foaming power, and free of irritation to the skin and the like, thus leading to completion of the present invention.

According to the present invention, there are thus provided an amine derivative represented by the following general formula (1):

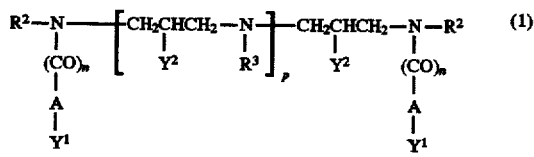

wherein $R^2$ and $R^3$ are identical with or different from each other and mean individually a linear or branched alkyl or alkenyl group which may be substituted by a hydroxyl group and has 1–24 carbon atoms, A denotes a linear or branched alkylene or alkenylene group which may be substituted by at least one hydroxyl, carboxyl or sulfonic group and has 1–6 carbon atoms, $Y^1$ is a carboxyl or sulfonic group, or a sulfuric acid residue, $Y^2$ means a hydroxyl group, a sulfuric acid residue or a group —OCO—A—COOH, n stands for a number of 0 or 1, and p is an integer of 1–8, or a salt or quaternized product thereof, and intermediates useful for the preparation thereof.

According to the present invention, there is also provided a detergent composition comprising this amine derivative (1), or a salt or quaternized product thereof.

As compounds having a structure close to that of the compounds according to the present invention, there have been known compounds having a 2-hydroxypropanediamine structure (U.S. Pat. No. 3,654,158, DE Patent No. 3,607,884, U.S. Pat. No. 4,982,000 and Japanese Patent Application Laid-Open Nos. 233264/1989 and 223515/1990, etc.). Since these compounds have a diamine structure and besides have no anionic functional groups such as a carboxyl group, a sulfonic group and a sulfuric acid residue, however, they cannot be used as detergent components. Therefore, they are greatly different from the compounds according to the present invention in both structure and function.

BEST MODE FOR CARRYING OUT THE INVENTION

Figure 1:
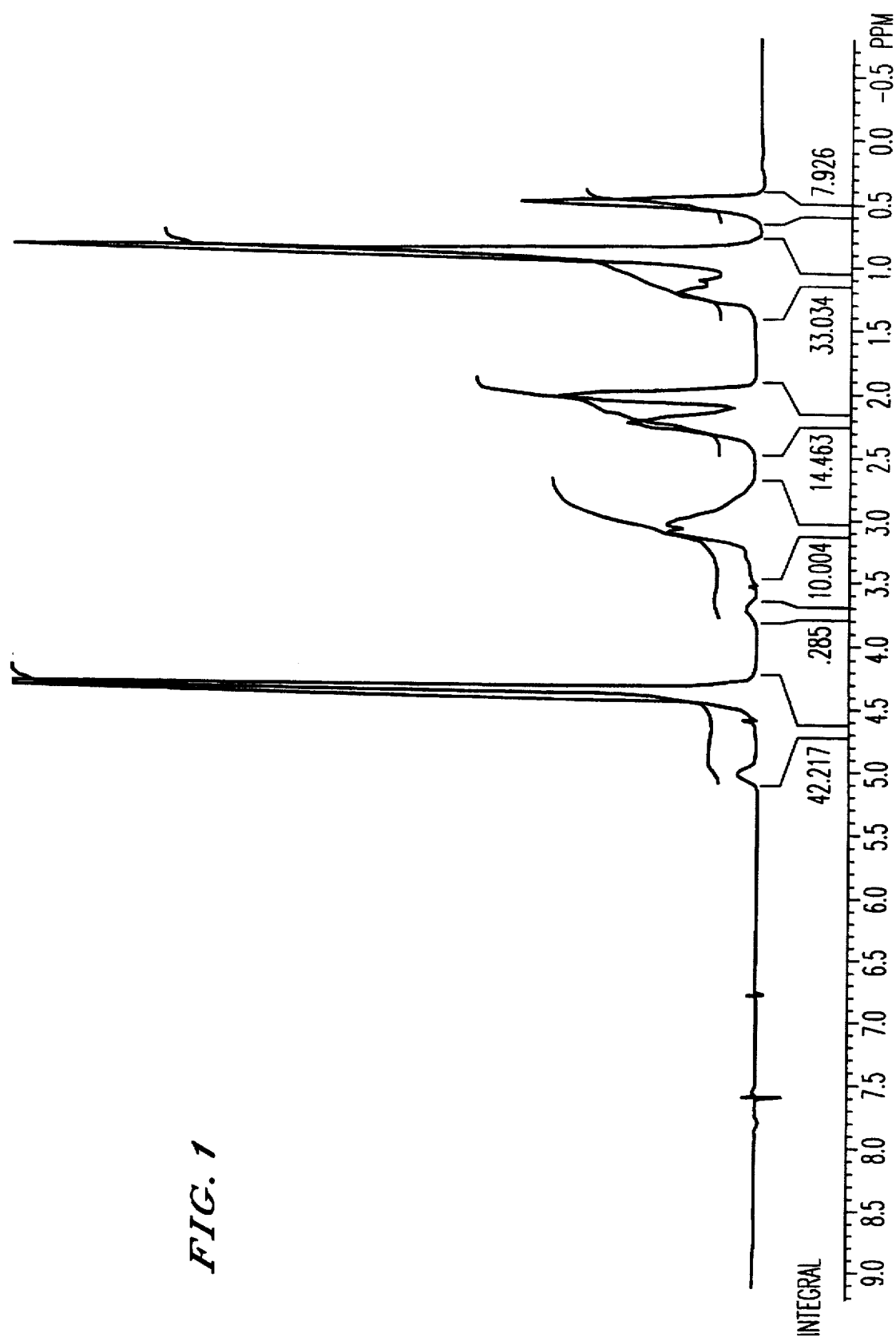
FIG. 1 illustrates an $^1$H-NMR spectrum of a compound of the present invention obtained in Example 7.

In the formula (1), specific examples of the linear or branched alkyl groups indicated by $R^2$ and $R^3$, which may be substituted by a hydroxyl group and have 1–24 carbon atoms, include the following compounds.

As the linear alkyl groups, may be mentioned methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. Examples of the branched alkyl groups include groups such as methylhexyl, ethylhexyl, methylheptyl, ethylheptyl, methylnonyl, methylundecyl, methylheptadecyl, hexyldecyl and octyldecyl.

As examples of the linear alkenyl groups, may be mentioned groups such as ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl and tetracosenyl. As examples of the branched alkenyl groups, may be mentioned groups such as methylhexenyl, ethylhexenyl, methylheptenyl, ethylheptenyl, methylnonenyl, methylundecenyl, methylheptadecenyl, hexyldecenyl and octyldecenyl.

With respect to the linear or branched alkyl group substituted by a hydroxyl group, no particular limitation is imposed on the position substituted by the hydroxyl group. Examples thereof include groups such as hydroxymethyl, hydroxyethyl, hydroxypropyl, hydroxybutyl, hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl, hydroxyoctadecyl, hydroxynonadecyl, hydroxyeicosyl, hydroxyheneicosyl, hydroxydocosyl, hydroxytricosyl, hydroxytetracosyl, hydroxymethylhexyl, hydroxyethylhexyl, hydroxymethylheptyl, hydroxyethylheptyl, hydroxymethylnonyl, hydroxymethylundecyl, hydroxymethylheptadecyl, hydroxyhexyldecyl and hydroxyoctyldecyl.

With respect to the linear or branched alkenyl group substituted by a hydroxyl group, no particular limitation is imposed on the position substituted by the hydroxyl group. Examples thereof include groups such as hydroxyethenyl, hydroxypropenyl, hydroxybutenyl, hydroxypentenyl, hydroxyhexenyl, hydroxyheptenyl, hydroxyoctenyl, hydroxynonenyl, hydroxydecenyl, hydroxyundecenyl, hydroxydodecenyl, hydroxytridecenyl, hydroxytetradecenyl, hydroxypentadecenyl, hydroxyhexadecenyl, hydroxyheptadecenyl, hydroxyoctadecenyl, hydroxynonadecenyl, hydroxyeicosenyl, hydroxyheneicosenyl, hydroxydocosenyl, hydroxytricosenyl, hydroxytetracosenyl, hydroxymethylhexenyl, hydroxyethylhexenyl, hydroxymethyl- heptenyl, hydroxyethylheptenyl, hydroxymethylnonenyl, hydroxymethylundecenyl, hydroxymethylheptadecenyl, hydroxyhexyldecenyl and hydroxyoctyldecenyl.

Among these, the linear or branched alkyl or alkenyl groups having 6–24 carbon atoms, particularly, the linear or branched alkyl groups having 6–12 carbon atoms, more particularly, the linear alkyl groups having 6–12 carbon atoms are preferred as $R^2$ and $R^3$.

In the formula (1), specific examples of the linear or branched alkylene or alkenylene groups indicated by A, which may be substituted by at least one hydroxyl, carboxyl or sulfonic group and has 1–6 carbon atoms, include the following compounds.

As examples of the alkylene or alkenylene group, may be mentioned methylene, ethylene, trimethylene, tetramethylene, pentamethylene, hexamethylene, methylethylene, ethylethylene, ethenylene, propenylene, butenylene, pentenylene and hexenylene groups. Of these, those having 1–4 carbon atoms are preferred and those having 1–3 carbon atoms are more preferred, with methylene, ethylene, trimethylene and ethenylene groups being particularly preferred.

These alkylene or alkenylene groups may be substituted by at least one hydroxyl group (—OH), sulfonic group (—SO₃H) or carboxyl group (—COOH). These substituent groups may be substituted either singly or in any combination of 2 to 4 groups of the same kind or different kinds.

Examples of the hydroxyl-substituted alkylene or alkenylene groups include 1-hydroxyethylene, 2-hydroxyethylene, 1,2-dihydroxyethylene, 1-hydroxytrimethylene, 2-hydroxytrimethylene, 3-hydroxytrimethylene, 1,2-dihydroxytrimethylene, 1,3-dihydroxytrimethylene, 1,2,3-trihydroxytrimethylene, 1-hydroxytetramethylene, 2-hydroxytetramethylene, 3-hydroxytetramethylene, 4-hydroxytetramethylene, 1,2-dihydroxytetramethylene, 1,3-dihydroxytetramethylene, 1,4-dihydroxytetramethylene, 2,3-dihydroxytetramethylene, 2,4-dihydroxytetramethylene, 3,4-dihydroxytetramethylene, 1,2,3-trihydroxytetramethylene, 2,3,4-trihydroxytetramethylene, 1,3,4-trihydroxytetramethylene and 1,2,3,4-tetrahydroxytetramethylene groups. Of these, 1,2-dihydroxyethylene, 1-hydroxyethylene, 2-hydroxyethylene and 2-hydroxytrimethylene groups are particularly preferred.

Examples of the sulfonic group-substituted alkylene or alkenylene groups include 1-sulfoethylene, 2-sulfoethylene, 1-sulfotrimethylene, 2-sulfotrimethylene, 3-sulfotrimethylene, 1-sulfotetramethylene, 2-sulfotetramethylene, 3-sulfotetramethylene, 4-sulfotetramethylene, 1,3-disulfotetramethylene, 1,4-disulfotetramethylene, 2,3-disulfotetramethylene and 2,4-disulfotetramethylene groups. Of these, 1-sulfoethylene and 2-sulfoethylene groups are particularly preferred.

Examples of the carboxyl group-substituted alkylene or alkenylene groups include 1-carboxyethylene, 2-carboxyethylene, 1-carboxytrimethylene, 2-carboxytrimethylene, 3-carboxytrimethylene and 1-carboxytetramethylene groups. Of these, 1-carboxyethylene and 2-carboxyethylene are preferred.

Examples of the alkylene or alkenylene groups substituted by hydroxyl and carboxyl groups include 2-carboxy-1-hydroxytrimethylene, 2-carboxy-1,3-dihydroxytrimethylene, 2-carboxy-2-hydroxytrimethylene and 3-carboxy-2,4-dihydroxytetramethylene groups. Of these, 2-carboxy-2-hydroxytrimethylene group is preferred.

Examples of the alkylene or alkenylene groups substituted by hydroxyl and sulfonic groups include 1-hydroxy-2-sulfoethylene, 2-hydroxy-1-sulfoethylene, 1-hydroxy-2-sulfotrimethylene, 1-hydroxy-3-sulfotrimethylene, 2-hydroxy-1-sulfotrimethylene, 2-hydroxy-3-sulfotrimethylene, 1,2-dihydroxy-3-sulfotrimethylene, 1,3-dihydroxy-2-sulfotrimethylene, 1-hydroxy-2-sulfotetramethylene, 1-hydroxy-4-sulfotetramethylene, 2-hydroxy-4-sulfotetramethylene and 3-hydroxy-4-sulfotetramethylene groups.

In the general formula (1), p stands for an integer of 1–8. However, p is preferably an integer of 1–5, with an integer of 1–3 being particularly preferred.

Since the compounds (1) according to the present invention have at least one sulfonic group (—SO₃H), sulfuric acid residue (—OSO₃H) or carboxyl group (—COOH), they can form salts with various basic substances. Examples of such salts include alkali metal salts, alkaline earth metal salts, amine salts, basic amino acid salts and ammonium salts. Specific examples thereof include salts with sodium, potassium, lithium, magnesium, calcium, trimethylamine, triethylamine, tributylamine, monoethanolamine, diethanolamine, triethanolamine, lysine, arginine, choline and ammonia. Of these, the alkali metal salts, particularly, the sodium salts are preferred. Incidentally, since the compounds (1) according to the present invention have tertiary amino groups, they may have a quaternary salt structure that a proton is coordinated on the nitrogen atom of the tertiary amino group, and so the tertiary amino group turns into an ammonium cation, and the sulfonic group, sulfuric acid residue or carboxyl group becomes a sulfonate anion (—SO₃⁻), a sulfate anion (—OSO₃⁻) or a carboxylate anion (—COO⁻) if n in the formula (1) is 0.

The compound (1) according to the present invention may be quaternized as needed. Specific examples thereof include compounds in which all or part of the nitrogen atoms in the formula (1) are quaternized. As examples of the group capable of bonding to the nitrogen atom for the quaternization, may be mentioned alkyl groups which may be substituted by at least one hydroxyl, carboxyl or sulfonic group and each have 1–6 carbon atoms, a benzyl group, and —(R⁴O)ₘH in which R⁴ denotes an alkylene group having 2–4 carbon atoms, and m stands for a number of 1–50. Here, examples of the alkyl groups which may be substituted by at least one hydroxyl, carboxyl or sulfonic group and has 1–6 carbon atoms include methyl, ethyl, propyl, isopropyl, butyl, pentyl, hexyl, hydroxyethyl, 1,2-dihydroxypropyl, carboxymethyl and 2-hydroxy-3-sulfopropyl groups. Specific examples of the group represented by the radical —(R⁴O) $_m$H include polyoxyethylene and polyoxypropylene groups. Of these groups, those in which m is 1–20 are preferred. The quaternized products of the compounds (1) according to the present invention may exist where n in the formula (1) is 0.

The compounds (1) according to the present invention are prepared in accordance with, for example, the following reaction schemes a to d:

[Reaction Scheme a]

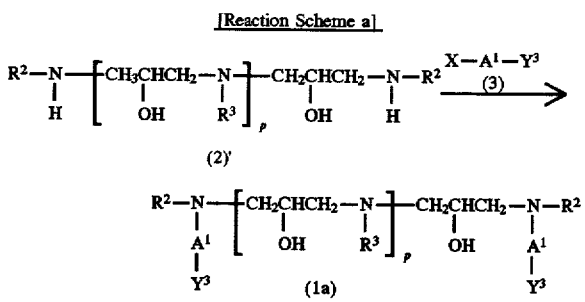

wherein $R^2$, $R^3$ and p have the same meaning as defined above, $A^1$ means an alkylene or alkenylene group which may be substituted by at least one hydroxyl or carboxyl group and has 1–6 carbon atoms, X denotes a halogen atom, and $Y^3$ stands for a sulfonic or carboxyl group.

More specifically, a compound (1a) according to the present invention is prepared by reacting a compound with a compound (2)' with a compound (3) or a salt thereof.

The reaction of the compound (2)' with the compound (3) or the salt thereof is conducted, for example, by reacting the compound (2)' with the compound (3) or the salt thereof in an amount of 2–5 moles per mole of the compound (2)' in the presence of an inert solvent at 20°–150° C., preferably 40°–100° C. while keeping pH 8–10. Examples of the halogen atom indicated by X in the compound (3) include chlorine, bromine and iodine atoms. Of these, the chlorine atom is more preferred. Specific examples of the compound (3) or salt thereof include sodium chloroacetate, sodium 3-chloro-2-hydroxypropanesulfonate, sodium 3-chloropropionate and sodium 4-chloro-n-butyrate. Of these, sodium chloroacetate and sodium 3-chloro-2-hydroxypropanesulfonate are more preferred. Examples of the inert solvent used herein include polar solvents such as water, methanol, ethanol, isopropyl alcohol, dimethylformamide and dimethyl sulfoxide, and the like. These solvents may be used either singly or in any combination thereof. However, water, a lower alcohol or a mixed solvent of water and a lower alcohol is preferred. Incidentally, when the compound (3) is used in excess of the amine derivative (2)' in this reaction, a compound according to the present invention, in which all or part of the nitrogen atoms in the formula (1a) are quaternized, is formed.

After completion of the reaction, the reaction mixture may contain, in addition to the intended compound (1a) according to the present invention, inorganic salts, an unreacted compound (2)', an addition compound of the compound (2)' and the compound (3) in an amount of 1 mole per mole of the compound (2)', and an unreacted compound (3) in some cases. In this case, the intended compound may be purified in the following manner except where the reaction mixture can be used as it is. As a purification method, may be used a method known Per se in the art, for example, solvent fractionation, ion exchange chromatography, recrystallization, electrodialysis or the like. Although the intended product obtained may be isolated as a free base, it may be subjected to salt exchange by a usual means such as neutralization with a desired basic substance, thereby isolating it in the form of the desired salt. Examples of the basic substance used herein include sodium hydroxide, potassium hydroxide, lithium hydroxide, magnesium hydroxide, calcium hydroxide, ammonia, trimethylamine, triethylamine, tributylamine, alkanolamines (monoethanolamine, diethanolamine, triethanolamine, etc.), lysine, arginine and choline. Of these, the hydroxides of alkali metals, such as sodium hydroxide and potassium hydroxide are preferred.

[Reaction Scheme b]

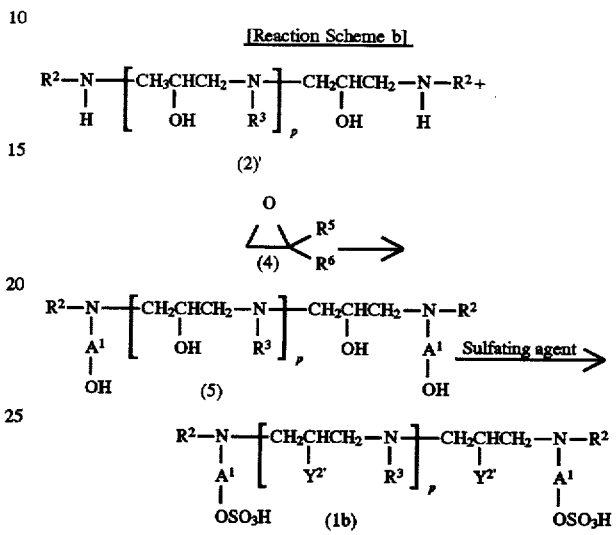

wherein $R^2$, $R^3$, $A^1$ and p have the same meaning as defined above, $R^5$ and $R^6$ are identical with or different from each other and mean individually a hydrogen atom, or an alkyl or alkenyl group which may be substituted by a hydroxyl or carboxyl group, and $Y^{2'}$ denotes a hydroxyl group or a sulfuric acid residue.

More specifically, a compound (1b) according to the present invention is prepared by reacting the compound (2)' with an epoxy compound (4), reacting the resulting compound (5) with a sulfating agent and optionally neutralizing the reaction product with a basic substance.

The reaction of the compound (2)' with the epoxy compound (4) is preferably conducted, for example, by reacting the compound (2)' with the epoxy compound (4) in an amount of 2–5 moles per mole of the compound (2)' in the presence of an inert solvent at preferably 100°–200° C., most preferably 130°–180° C. No particular limitation is imposed on the inert solvent used in this reaction so far as it is an aprotic solvent. However, lower hydrocarbons, aromatic hydrocarbons, ethers, halogenated hydrocarbons and the like are preferred in view of price and solubility. This reaction is preferably performed in a pressure vessel such as an autoclave in view of the boiling points of the epoxy compound (4) and the inert solvent used. The epoxy compound (4) is preferably ethylene oxide or propylene oxide because it is cheap, with ethylene oxide being particularly preferred.

The subsequent reaction of the thus-obtained compound (5) with the sulfating agent such as ClSO₃H or SO₃ is preferably conducted in a temperature range of from –75° C. to 150° C. in an inert solvent or without any solvent. The amount of ClSO₃H or SO₃ to be used is preferably 2 to (p+5) moles per mole of the compound (5). In the neutralization which is optionally conducted after completion of this reaction, the same basic substance as that used in Reaction Scheme a may be used.

In the first stage of the above Reaction Scheme b, compounds in which only one of the nitrogen atoms situated at both terminals of reactive sites has been reacted are also formed. Besides, in the sulfation of the second stage, compounds in which only part of the (p+3) hydroxyl groups have been sulfated are also formed. Such a reaction mixture may be used in various applications as it is. However, if a higher-purity product is required, it may be purified for use by a method known Per se in the art, for example, recrystallization, column chromatography, distillation or the like.

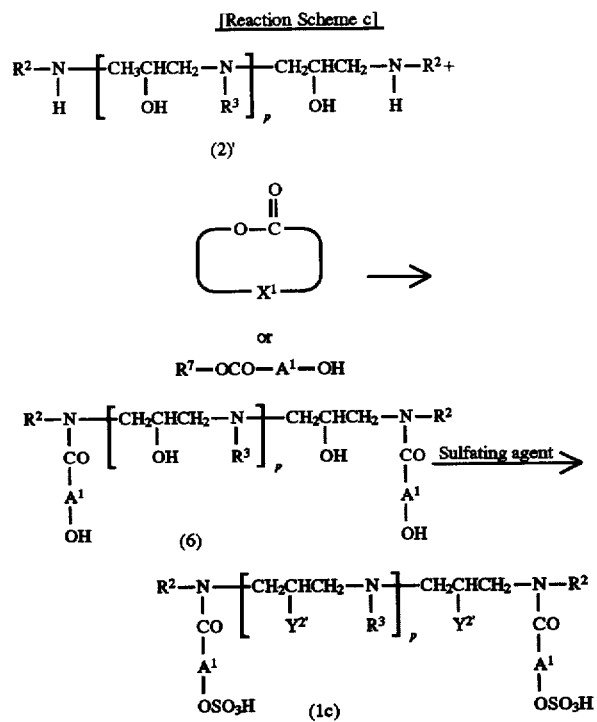

The reaction of the compound (2)' with the lactone or hydroxycarboxylic acid is preferably conducted, for example, by reacting the compound (2)' with the lactone or hydroxycarboxylic acid in an amount of 2–5 moles per mole of the compound (2)' in an inert solvent or without any solvent at preferably 20°–180° C., most preferably 40°–150° C. No particular limitation is imposed on the inert solvent used in this reaction so far as it is an aprotic solvent. However, lower hydrocarbons, aromatic hydrocarbons, ethers, halogenated hydrocarbons and the like are preferred in view of price and solubility. As the lactone and hydroxycarboxylic acid used in this reaction, γ-lactone, δ-lactone, glycolic acid, lactic acid, α-hydroxy acid and the methyl ester and ethyl ester thereof, and the like are preferred because they are cheap.

The reaction of the thus-obtained amidoalcohol (6) with the sulfating agent such as $ClSO_3H$ or $SO_3$ is preferably conducted in a temperature range of from –75° C. to 150° C. in an inert solvent or without any solvent. The amount of $ClSO_3H$ or $SO_3$ to be used is preferably 2 to (p+5) moles per mole of the amidoalcohol (6). The neutralization which is optionally conducted after completion of this reaction may be performed in the same manner as in Reaction Schemes a and b.

In the amidation of the first stage of the above Reaction Scheme c, compounds in which only one of the nitrogen atoms situated at both terminals of reactive sites has been reacted are also formed. Besides, in the sulfation of the second stage, compounds in which only part of the (p+3) hydroxyl groups have been sulfated are also formed. Such a reaction mixture may be used in various applications as it is. However, if a higher-purity product is required, it may be purified for use by a method known per se in the art, for example, recrystallization, column chromatography, distillation or the like.

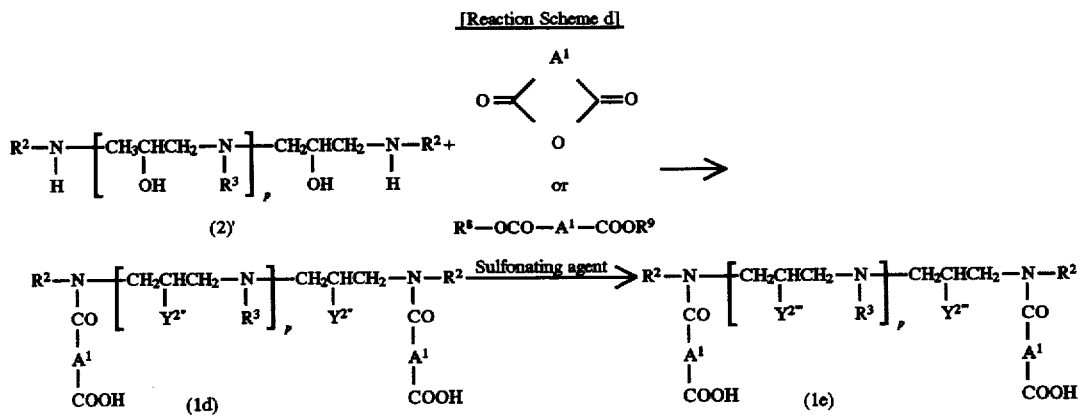

wherein $R^2$, $R^3$, $A^1$, $Y^{2'}$ and p have the same meaning as defined above, and $R^7$ means a hydrogen atom or an alkyl group which may have a substituent group.

More specifically, a compound (1c) according to the present invention is prepared by reacting the compound (2)' with a lactone or a hydroxycarboxylic acid, reacting the resulting amidoalcohol (6) with a sulfating agent and optionally neutralizing the reaction product with a basic substance.

wherein $R^2$, $R^3$, $A^1$ and p have the same meaning as defined above, $R^8$ and $R^9$ mean individually a hydrogen atom, or an alkyl or alkenyl group which may have a substituent group, $A^2$ denotes a linear or branched alkylene group which may be substituted by a hydroxyl or carboxyl group, has been substituted by a sulfonic group and has 1–6 carbon atoms, $Y^{2''}$ stands for a hydroxyl group or —OCO—$A^1$—COOH, and $Y^{2'''}$ is a hydroxyl group or —OCO—$A^2$—COOH.

More specifically, a compound (1d) according to the present invention or a salt thereof can be prepared by reacting the compound (2)' with an acid anhydride, or a dicarboxylic acid or an ester thereof, further hydrolyzing the reaction product if the ester is used, and optionally neutralizing the reaction product or the hydrolyzate with a basic substance. In the case where —CH═CH— is contained in $A^1$ of the resultant compound (1d), a compound (1e) according to the present invention is further prepared by reacting the compound (1d) with a sulfonating agent such as $SO_3$, sodium sulfite or $NaHSO_3$, and optionally neutralizing the reaction product with a basic substance.

The reaction of the compound (2)' with the acid anhydride is preferably conducted, for example, by reacting the compound (2)' with the acid anhydride in an amount of preferably 2.0 to (p+5) moles per mole of the compound (2)' in the presence of a water-free inert solvent at 20°–150° C., preferably 40°–100° C. Examples of the water-free inert solvent used herein include ethers, tetrahydrofuran, benzene and pyridine. In this reaction, if the acid anhydride is used in a great amount, all or part of the (p+1) hydroxyl groups in the compound (2)' react with the acid anhydride into their corresponding number of groups —OCO—$A^1$—COOH.

Besides, the reaction of the compound (2)' with the dicarboxylic acid or ester thereof is preferably conducted, for example, by reacting the compound (2)' with the dicarboxylic acid or ester thereof in an amount of preferably 2.0–5.0 moles per mole of the compound (2)' in the presence of an inert solvent at 40°–180° C., preferably 80°–150° C. This reaction is preferably performed while removing an alcohol or water formed. Examples of the inert solvent used in this reaction include hexane, benzene, toluene and xylene.

Incidentally, examples of the alkyl or alkenyl groups indicated by $R^8$ and $R^9$ in the formula of the dicarboxylic ester include those having 1–5 carbon atoms. Of these, methyl and ethyl groups are preferred.

In this reaction, an intermediate represented by the following general formula (7) is formed if the dicarboxylic ester is used. It is hence necessary to subsequently hydrolyze the intermediate in the presence of an acid or basic catalyst in, for example, a water-containing alcohol.

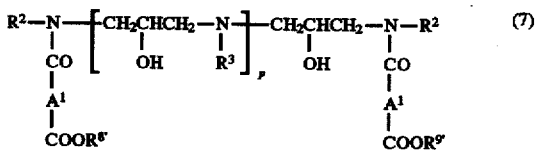

wherein $R^2$, $R^3$, $A^1$ and p have the same meaning as defined above, and $R^{8'}$ and $R^{9'}$ mean alkyl or alkenyl groups corresponding to $R^8$ and $R^9$, respectively.

Then, the reaction of the compound (1d) containing —CH═CH— in $A^1$ with the sulfonating agent such as $SO_3$, sodium sulfite or sodium hydrogensulfite is preferably conducted, for example, by reacting the compound (1d) with $SO_3$, sodium sulfite or sodium hydrogensulfite in an amount of 1.0–6.0 moles, preferably 1.0–3.0 moles per mole of the —CH═CH— group in the compound (1d) at pH 4.0–11.0, preferably 5.0–8.0 and 30°–100° C., preferably 40°–80° C. in water.

The neutralization of the thus-obtained compounds (1d) and (1e) according to the present invention may be performed in the same manner as in Reaction Schemes a–c. In these reactions, compounds in which only one of the amino groups situated at both terminals has been amidated, and the like are formed as by-products. However, such reaction mixtures may be used in various applications as they are.

However, if higher-purity products are required, they may be purified for use by a method known per se in the art, for example, recrystallization, column chromatography, electrodialysis or the like.

When one of the thus-obtained compounds (1) according to the present invention is reacted with a quaternizing agent, a compound in which all or part of the (p+2) nitrogen atoms when n in the general formula (1) is 0, or of the nitrogen atoms in p tertiary amino groups when n is 1 have been quaternized is obtained.

Examples of the quaternizing agent include alkyl halides which may be substituted by a hydroxyl, carboxyl or sulfonic group and have 1–6 carbon atoms, benzyl halides and alkylene oxides or salts thereof. Of these, the alkyl halides are more preferred. Examples of the alkyl group in these compounds include methyl, ethyl, n-propyl, n-butyl and isopropyl groups. Examples of the halogen include chlorine, bromine and iodine. Of these compounds, methyl chloride is particularly preferred.

The amine derivative (2)' used as a raw material for the compounds (1) according to the present invention in Reaction Schemes a to d can be prepared in accordance with, for example, the following reaction scheme.

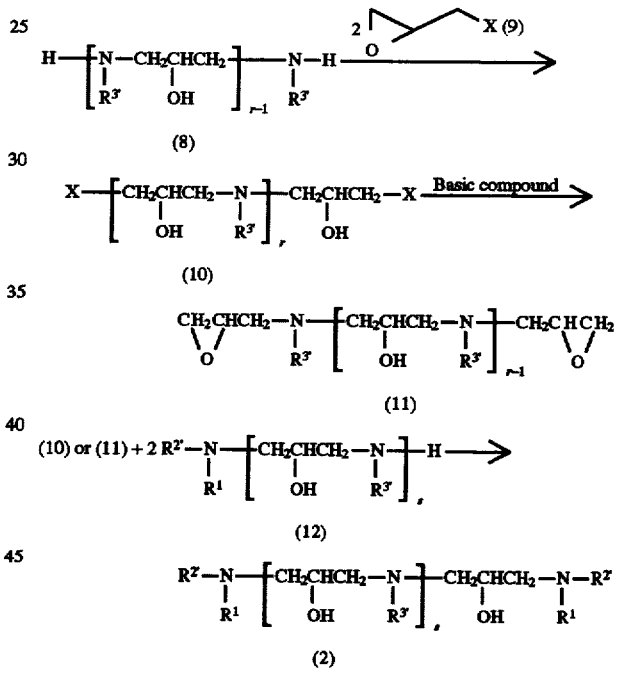

wherein X and p have the same meaning as defined above, $R^1$, $R^{2'}$ and $R^{3'}$ are identical with or different from one another and mean individually a hydrogen atom, or a linear or branched alkyl or alkenyl group which may be substituted by a hydroxyl group and has 1–24 carbon atoms, and r and s stand for integers of 1–8 and 0–2, respectively, with the proviso that r and s satisfy the relationship of 2s+r=p.

More specifically, an amine derivative (2) is obtained by reacting a halohydrin compound (10) obtained by reacting an amine derivative (8) with an epihalohydrin (9), or an epoxy compound (11) obtained by reacting the halohydrin compound (10) with a basic compound, with an amine derivative (12). In the amine derivatives represented by the general formula (2), a compound in which $R^1$ in the general formula (2) is a hydrogen atom, and $R^{2'}$ and $R^{3'}$ are $R^2$ and $R^3$, respectively, is the amine derivative (2)'. In the amine derivative (2)', it is preferred that $R^2$ and $R^3$ be individually a linear or branched alkyl or alkenyl group having 6–24 carbon atoms, more preferably a linear or branched alkyl group having 6–12 carbon atoms, most preferably a linear alkyl group having 6–12 carbon atoms.

Incidentally, in the amine derivatives (2), other compounds than those in which in the case where p is 1 in the general formula (2), $R^{3'}$ is a hydrogen atom, or an alkyl or alkenyl group substituted by no hydroxyl group, and $R^1$ and $R^{2'}$ are individually a hydrogen atom, or an alkyl or alkenyl group which may be substituted by a hydroxyl group and has 1–5 carbon atoms are novel compounds undescribed in the literature. According to the present invention, there are also provided these novel amine derivatives (2).

In the preparation process, examples of the halogen atom indicated by X in the epihalohydrin (9) used in the synthesis of the halohydrin compound (10) include chlorine, bromine and iodine atoms, with chlorine being preferred.

The reaction of the amine derivative (8) with the epihalohydrin (9) may be conducted, for example, without any solvent or in a solvent inert to the reaction, such as a lower alcohol, an ether, an aromatic hydrocarbon or a mixture thereof at a temperature of preferably –20° to 100° C., more preferably 0° to 60° C. The proportion of the amine derivative (8) and epihalohydrin (9) to be used may be suitably preset. However, it is preferable to use the epihalohydrin (9) in an amount of 2–5 moles per mole of the amine derivative (8).

Preferable examples of the basic compound used in the subsequent synthesis of the epoxy compound (11) include the hydroxides of alkali metals, the carbonates of alkali metals and amines. Sodium hydroxide and potassium hydroxide are particularly preferred.

The reaction of the halohydrin compound (10) with the basic compound may be conducted, for example, in a solvent inert to the reaction, such as water, a lower alcohol or a mixture thereof at preferably 0°–80° C., more preferably 20°–60° C. The proportion of the halohydrin compound (10) and basic compound to be used may be suitably preset. However, it is preferable to use the basic compound in an amount of 2–5 moles per mole of the halohydrin compound (10).

The reaction of the halohydrin compound (10) or epoxy compound (11) obtained in the above-described manner with the amine derivative (12) may be conducted, for example, without any solvent or in a solvent inert to the reaction, such as a lower alcohol, an ether, an aromatic hydrocarbon or a mixture thereof at preferably 40°–150° C., more preferably 60°–100° C. The proportion of the respective compounds to be used in the reaction may be suitably preset. However, it is preferable to use the amine derivative (12) in an amount of 2–20 moles, particularly 2–10 moles per mole of the halohydrin compound (10) or the epoxy compound (11).

By such reactions, the amine derivatives (2) according to the present invention can be obtained. In addition to the intended compounds, however, there may be secondarily formed or left salts of an amine and an acid, inorganic salts, unreacted respective compounds, etc. according to the reaction conditions and the like. In the present invention, the reaction mixtures may be used as they are. However, as needed, they may be more purified by a method known per se in the art, such as solvent fractionation, dialysis, recrystallization, distillation, partition chromatography or gel filtration.

Among the amine derivatives (2) thus obtained, compounds (2)' in which $R^1$, $R^{2'}$ and $R^{3'}$ in the general formula (2) are a hydrogen atom, $R^2$ and $R^3$, respectively, are useful as raw materials in the preparation of the compounds (1) of the present invention according to Reaction Schemes a–d as described above. Besides, even from a compound in which neither $R^1$ nor $R^{2'}$ in the general formula (2) is a hydrogen atom, a compound according to the present invention, which is a quaternized product represented by the following general formula (1a)', can be prepared in one stage by reacting this compound with the compound (3). Therefore, such amine derivatives are also useful as raw materials for the quaternized products.

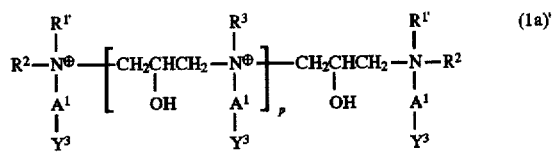

wherein $R^2$, $R^3$, $A^1$, $Y^3$ and p have the same meaning as defined above, and $R^{1'}$ means an alkyl or alkenyl group corresponding to $R^1$.

Incidentally, the amine derivatives (2) are also excellent in corrosion-inhibiting ability for metals. Therefore, they are also useful as additive components for fuel oils and lubricating oil additives for gasoline or diesel engines, and can prevent metals from corroding without lowering the performance of engine oil and the like.

The amine derivatives according to the present invention, which are represented by the general formula (1), have excellent detergency and foaming power and hence can be used in applications making good use of these properties, for example, various detergents such as skin and hair detergents, dishwashing detergents, and laundry detergents. No particular limitation is imposed on the amount of the compound (1) according to the present invention to be incorporated in that case. However, it may be used in a range of 0.1–80 wt. %, preferably 1–50 wt. % according to the intended application thereof, and the like.

These detergent compositions according to the present invention may optionally contain various known surfactants, moisturizers, germicides, emulsifying agents, thickeners, pearly luster-imparting agents, divalent metal ion sequestrants, alkalifying agents, inorganic salts, resoiling preventives, enzymes, available chlorine scavengers, reducing agents, bleaching agents, fluorescent dyes, solubilizing agents, perfume bases, caking preventives, enzyme activators, antioxidants, antiseptics, coloring matter, bluing agents, bleaching activators, enzyme stabilizers, phase modifiers, penetrating agents, and the like.

As the surfactants, may be used anionic surfactants, nonionic surfactants, amphoteric surfactants and cationic surfactants. The anionic surfactants are usually incorporated for the purpose of improving detergency, foaming power and a feel upon use. Examples thereof include higher fatty acid salts, alkylsulfates, alkyl ether sulfates, alkylsulfonates, α-olefinsulfonates, alkylbenzenesulfonates, alkanoylisethionates, alkylsuccinates, alkylsulfosuccinates, N-alkanoylsarcosinates, alkylphosphates, alkyl ether phosphates and alkyl ether carboxylates. The alkyl and acyl groups of these anionic surfactants generally have 8–20 carbon atoms, and may be converted to unsaturated groups. The alkyl ether sulfates, alkyl ether phosphates and alkyl ether carboxylates may contain 1–10 ethylene oxide or propylene oxide units per molecule. However, they preferably contain 2–3 ethylene oxide units per molecule. Examples of the salts of these anionic surfactants include the sodium, magnesium, ammonium and mono-, di- and triethanolamine salts.

The nonionic surfactants are usually incorporated for the purpose of improving detergency and a feel upon use.

Examples thereof include polyoxyalkylene alkyl ethers, polyoxyalkylene phenyl ethers, mono- or dialkylalkanolamides or alkylene oxide adducts thereof, alkyl polyglycosides and monoglycerides. The alkyl and acyl groups of these nonionic surfactants generally have 8–20 carbon atoms, and may be converted to unsaturated groups. The polyoxyalkylene groups thereof include polyoxyethylene, polyoxypropylene and a mixed type thereof, and their condensation degree is generally 6–30.

Examples of the amphoteric surfactants include long-chain-alkyl-dimethylcarboxymethylbetaines and sulfobetaines. Examples of the cationic surfactants include long-chain alkyl-trimethylammonium salts and di-long-chain-alkyl-dimethylammonium salts.

These surfactants are incorporated in combination with the compound (1) according to the present invention in an amount of 0.5–60 wt. % of the detergent composition. In particular, when the detergent composition is provided in the form of powder, they are preferably incorporated in an amount of 10–45 wt. %. When the detergent composition is provided in the form of liquid, they are preferably incorporated in an amount of 20–50 wt. %. Further, when the detergent composition is provided as a bleaching detergent, the surfactants are preferably incorporated in an amount of generally 1–10 wt. %, more preferably 1–5 wt. %.

As the moisturizers, may be used glycerin, ethylene glycol, propylene glycol, 1,3-butylene glycol and the like.

As the thickeners, may be used polyacrylic acid, crosslinked polymers of acrylic acid, copolymers of acrylic acid and a hydrophobic monomer, copolymers of a carboxylic acid-containing monomer and an acrylic ester, crosslinked copolymers of acrylic acid and an acrylic ester, ethylene glycol ester or polyethylene glycol ester (for example, fatty acid ester thereof), and heteropolysaccharide gums.

The pearly luster-imparting agents may be selected from $C_{16-22}$ fatty acids, $C_{16-22}$ esters of a fatty acid and an alcohol, and $C_{16-22}$ fatty acid esters containing elements such as alkylene glycol units. Examples of suitable alkylene glycol units include ethylene glycol and propylene glycol. However, polyalkylene glycols may also be used. Examples of suitable polyalkylene glycols include polyethylene glycol and polypropylene glycol.

As the divalent metal ion sequestrants, may be used condensed phosphates such as tripolyphosphates, pyrophosphates and orthophosphates, aluminosilicates such as zeolite, synthetic layer lattice silicates, nitrilotriacetates, ethylenediaminetetraacetates, citrates, isocitrates, polyacetalcarboxylates and the like.

The divalent metal ion sequestrants are incorporated in an amount of 0–50 wt. %, preferably 5–40 wt. %. It is more preferable to use a divalent metal ion sequestrant containing no phosphorus.

As the alkalifying agents and inorganic salts, are used silicates, carbonates, sesquicarbonates, sulfates, alkanolamines and the like. These components are incorporated in an amount of 0–80 wt. %.

As the resoiling preventives, are used polyethylene glycol, polyacrylates, acrylic acid copolymers such as acrylic acid-maleic acid copolymers, polyvinyl alcohol, polyvinyl pyrrolidone, carboxymethylcellulose and the like. Part of the resoiling preventives may also be used as divalent metal ion sequestrant. The resoiling preventives are incorporated in an amount of 0–10 wt. %, preferably 1–5 wt. %.

As the enzymes, may be used cellulase, α-amylase, pullulanase, lipase, hemicellulase, β-glycosidase, glucose oxidase, cholesterol oxidase, protease and the like.

Examples of the scavengers for available chlorine in tap water include ammonium sulfate, urea, guanidine hydrochloride, guanidine carbonate, guanidine sulfamate, thiourea dioxide, monoethanolamine, diethanolamine, triethanolamine, glycine, amino acids typified by sodium glutamate and proteins such as bovine serum albumin and casein, and besides hydrolyzates of proteins, meat extracts and fish meat extracts. Examples of the reducing agents include alkali metal salts and alkaline earth metal salts such as the thiosulfates, sulfites and dithionites thereof, and Rongalit C. The sulfites are particularly preferred and serve to stabilize the enzymes in washing liquid.

Examples of the bleaching agent include percarbonates, perborates, zinc or aluminum sulfonated phthalocyanine, and hydrogen peroxide. When they are used in a bleaching detergent, sodium peroxide is particularly effective. Its amount to be incorporated is preferably 1–95 wt. %, more preferably 5–95 wt. %, most preferably 20–95 wt. %.

Examples of the fluorescent dyes include fluorescent dyes used generally in detergents. In the case of a liquid detergent, a solubilizing agent, for example, a lower alcohol such as ethanol, a benzenesulfonate, a lower alkylbenzenesulfonate such as p-toluenesulfonate, glycerin, or a polyol such as propylene glycol may be incorporated.

The detergent compositions according to the present invention can be prepared by using the compound (1) according to the present invention in combination with the above-described known components in accordance with a method known per se in the art. The form of the detergents may be selected according to the intended application, and the detergents may be prepared in the form of, for example, liquid, powder or granules.

EXAMPLES

The present invention will hereinafter be described in more detail by the following examples. However, it should be born in mind that the invention is not limited to these examples.

Example 1

A reactor was charged with 286.3 g (1.54 moles) of dodecylamine and 90 g of xylene, and the contents were heated to 80° C. To the contents, a solution with 57 g (0.15 mole) of N,N-bis(3-chloro-2-hydroxypropyl)dodecylamine dissolved in 50 g of xylene was added dropwise over 1.5 hours. The resultant mixture was aged further for 4 hours. Thereafter, xylene was distilled off under reduced pressure, and unreacted dodecylamine was then distilled off at 100° C. and 0.5 mmHg. The residue was added with 500 ml of hexane and 2000 ml of acetone to be dissolved therein. The solution was then subjected to extraction and washing with a mixture of 500 ml of xylene and 500 ml of 5% aqueous sodium hydroxide. Thereafter, a xylene layer was taken out and concentrated, thereby obtaining 49.5 g (yield: 48%) of 15,19-dihydroxy-17-dodecyl-13,17,21-triazatritriacontane represented by the following formula.

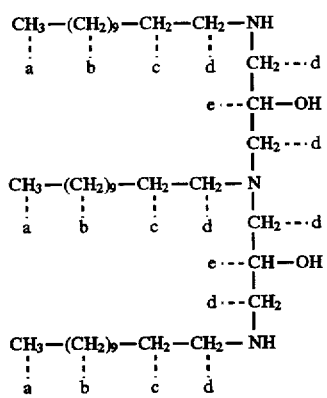

Mass spectrometry (FAB ionization method): m/z: 669 (M+H$^+$), m=$C_{42}H_{89}N_3O_2$.

$^1$H-NMR (CDCl$_3$, δ ppm): 0.88 (t,9H,(a)), 1.28 (broad, 54H,(b)), 1.45 (broad,6H, (c)), 2.45–2.73 (broad m,12H,(d)), 3.74 (m,2H,(e)).

Example 2

A reactor was charged with 371 g (2.87 moles) of octylamine, and the contents were heated to 70° C. To the contents, a solution with 70 g (0.27 mole) of N,N-bis(3-chloro-2-hydroxypropyl)butylamine dissolved in 50 g of xylene was then added dropwise over 40 minutes. The resultant mixture was aged further for 4 hours. Thereafter, xylene was distilled off under reduced pressure, and unreacted octylamine was then distilled off at 70° C. and 0.5 mmHg. A mixture of 400 ml of xylene and 400 ml of 5% aqueous sodium hydroxide was added to the residue to subject it to extraction and washing. Thereafter, a xylene layer was taken out and concentrated, thereby obtaining 99.8 g (yield: 82%) of 11,15-dihydroxy-13-butyl-9,13,17-triazapentacosane represented by the following formula.

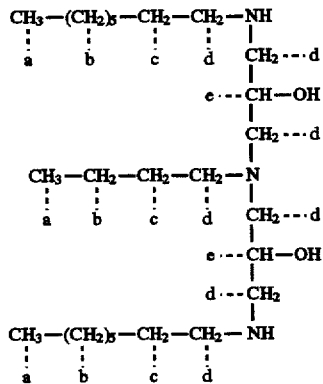

Mass spectrometry (FAB ionization method): m/z: 445 (M+H$^+$), m=$C_{26}H_{57}O_2N_3$.

$^1$H-NMR (CDCl$_3$, δ ppm): 0.85 (t,9H,(a)), 1.22 (broad, 22H,(b)), 1.26–1.33 (broad,6H,(c)), 2.40–2.71 (broad m,14H,(d)), 3.77 (m,2H,(e)).

Example 3

A reactor was charged with 280 g (1.51 moles) of dodecylamine and 100 g of xylene, and the contents were heated to 70° C. To the contents, a solution with 38.5 g (0.18 mole) of N,N-bis(3-chloro-2-hydroxypropyl)hydroxyethylamine dissolved in 20 g of xylene was added dropwise over 30 minutes. The resultant mixture was aged further for 4 hours. Thereafter, xylene was distilled off under reduced pressure, and unreacted dodecylamine was then distilled off at 100° C. and 0.5 mmHg. The residue was subjected to extraction and washing with a mixture of 500 ml of hexane and 500 ml of 5% aqueous sodium hydroxide. Thereafter, a hexane layer was taken out and concentrated, thereby obtaining 75.6 g (yield: 77%) of 15,19-dihydroxy-17-hydroxyethyl-13,17,21-triazatritriacontane represented by the following formula.

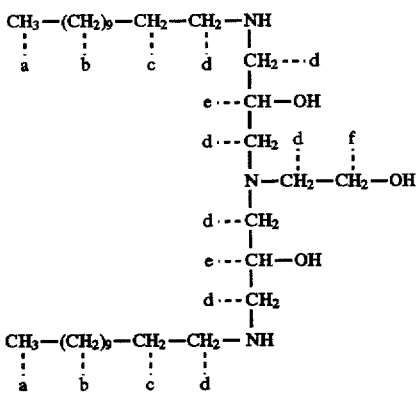

Mass spectrometry (FAB ionization method): m/z: 545 (M+H$^+$), m=$C_{32}H_{69}O_3N_3$.

$^1$H-NMR (CDCl$_3$, δ ppm): 0.88 (t,6H,(a)), 1.25 (broad, 36H,(b)), 1.29 (broad,4H, (c)), 2.41–2.80 (broad m,14H,(d)), 3.39 (broad t,2H,(f)), 3.75 (m,2H,(e)).

Example 4

A reactor was charged with 275 g (2.2 moles) of octylamine, and the contents were heated to 70° C. To the contents, a solution with 36 g (0.17 mole) of N,N-bis(3-chloro-2-hydroxypropyl)hydroxyethylamine dissolved in 30 g of xylene was then added dropwise over 40 minutes. The resultant mixture was aged further for 4 hours. Thereafter, xylene was distilled off under reduced pressure, and unreacted octylamine was then distilled off at 70° C. and 0.5 mmHg. A mixture of 500 ml of xylene and 500 ml of 5% aqueous sodium hydroxide was added to the residue to subject it to extraction and washing. Thereafter, a xylene layer was taken out and concentrated, thereby obtaining 50.7 g (yield: 69%) of 11,15-dihydroxy-13-hydroxyethyl-9,13,17-triazapentacosane represented by the following formula.

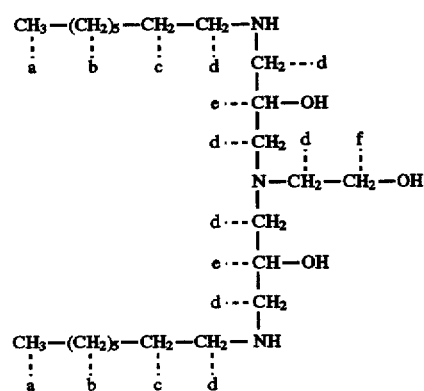

Mass spectrometry (FAB ionization method): m/z: 432, m=$C_{24}H_{53}O_3N_3$.

¹H-NMR (CDCl₃, δ ppm): 0.86 (t,6H,(a)), 1.25 (broad, 20H,(b)), 1.27 (broad,4H,(c)), 2.40–2.80 (broad m,14H,(d)), 3.41 (broad t,2H,(f)), 3.77 (m,2H,(e)).

All the amine derivatives obtained in Examples 1–4 had excellent corrosion-inhibiting ability for metals.

Synthesis Example 1

A reactor was charged with 16.6 g (0.025 mole) of 15,19-dihydroxy-17-dodecyl-13,17,21-triazatritriacontane obtained in Example 1 and 200 g of xylene, and the contents were kept at 50° C. To the contents, 6.9 g (0.075 mole) of epichlorohydrin was added dropwise over one hour and ten minutes, and the resultant mixture was aged for 36 hours. Thereafter, the solvent and unreacted epichlorohydrin were distilled off under reduced pressure at room temperature, thereby obtaining 21.2 g of 15,19-dihydroxy-13,21-bis(3-chloro-2-hydroxypropyl)-17-dodecyl-13,17,21-triazatritriacontane represented by the following formula.

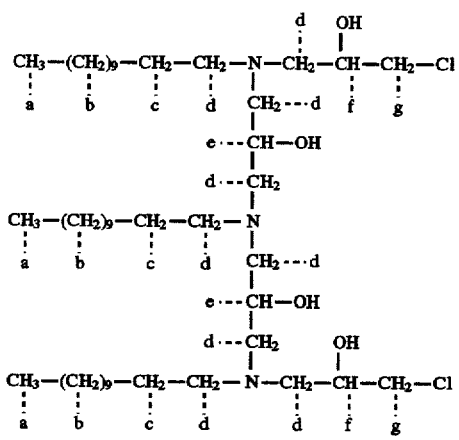

¹H-NMR (CDCl₃, δ ppm): 0.90 (t,9H,(a)), 1.25 (br,54H, (b)), 1.45 (br,6H,(c)), 2.46–2.80 (br,m,18H,(d)), 3.58 (m,4H, (g)), 3.75 (m,2H,(e)), 3.90 (m,2H,(f)).

Mass spectrometry (FAB ionization method): m/z: 852 (M+H⁺), m=$C_{48}H_{99}N_3O_4Cl_2$.

Synthesis Example 2

A reactor was charged with 5 g (5.9 millimoles) of 15,19-dihydroxy-13,21-bis(3-chloro-2-hydroxypropyl)-17-dodecyl-13,17,21-triazatritriacontane obtained in Synthesis Example 1, 20 g of ethanol and 10 g of water, and the contents were kept at 50° C. To the contents, 1.8 ml of 1N aqueous sodium hydroxide was added to stir the resultant mixture for 20 minutes. The solvent was then distilled off under reduced pressure, and 50 ml of ethanol was added to the residue to filter out insoluble matter. Thereafter, ethanol was distilled off under reduced pressure, thereby obtaining 4.6 g of 13,17,21-triaza-17-dodecyl-13,21-bis(2,3-epoxypropyl)-15,19-dihydroxytritriacontane represented by the following formula.

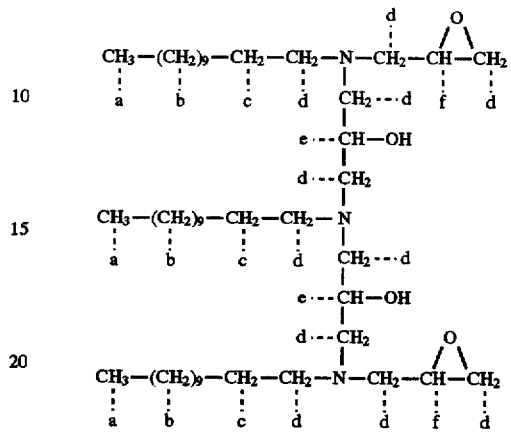

¹H-NMR (CDCl₃, δ ppm): 0.95 (t,9H,(a)), 1.31 (br,54H, (b)), 1.44 (br,6H,(c)), 2.44–2.82 (m,22H,(d)), 3.15 (m,2H, (f)), 3.77 (m,2H, (e)).

Mass spectrometry (FAB ionization method): m/z: 779 (M+H⁺), m=$C_{48}H_{97}N_3O_4$.

Example 5

A reactor was charged with 77 g (0.42 mole) of dodecylamine and 100 g of ethanol, and the contents were heated to 75° C. To the contents, a solution with 21.2 g (0.025 mole) of 15,19-dihydroxy-13,21-bis(3-chloro-2-hydroxypropyl)-17-dodecyl-13,17,21-triazatritriacontane obtained in Synthesis Example 1 dissolved in 50 g of ethanol was added dropwise over 30 minutes. The resultant mixture was aged further for 5 hours. Thereafter, ethanol was distilled off under reduced pressure, and unreacted dodecylamine was then distilled off at 100° C. and 0.5 mmHg. The residue was subjected to extraction and washing with a mixture of 500 ml of hexane and 500 ml of 5% aqueous sodium hydroxide. A hexane layer was taken out and concentrated, thereby obtaining 21.1 g (yield: 73.5%) of 15,19,23,27-tetrahydroxy-17,21,25-tridodecyl-13,17,21,25,29-pentaazahentetracontane represented by the following formula.

This compound had excellent corrosion-inhibiting ability for metals and was useful as a detergent for fuel oils such as gasoline and gas oil and a lubricant oil additive for gasoline and diesel engines.

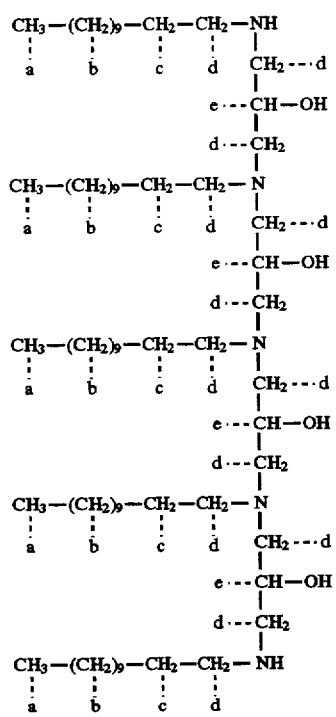

¹H-NMR (CDCl₃, δ ppm): 0.82 (t,16H,(a)), 1.22 (br,90H, (b)), 1.35 (br,10H,(c)), 2.35, 2.60 (br,m,26H,(d)), 3.67 (br, m,4H,(e)).

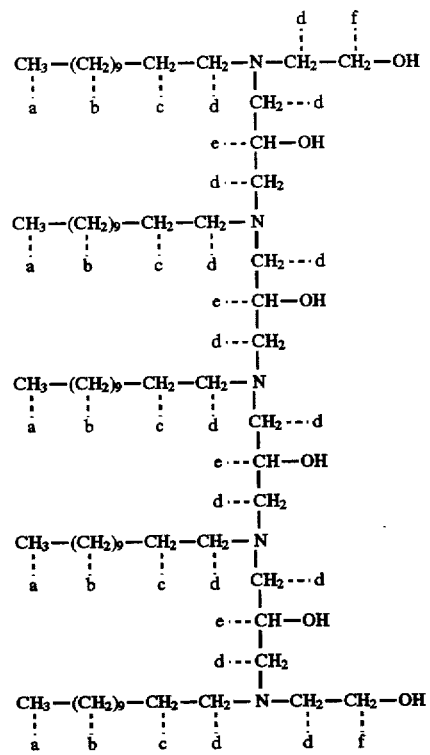

¹H-NMR (CDCl₃, δ ppm): 0.88 (t,15H,(a)), 1.28 (br,90H, (b)), 1.42 (br,10H,(c)), 2.40–2.61 (br,m,30H,(d)), 3.58 (br, m,4H,(e)), 3.70 (br,m,4H,(f)).

Example 6

A reactor was charged with 35 g (0.15 mole) of N-hydroxyethyl-dodecylamine and 50 g of ethanol, and the contents were heated to 75° C. To the contents, a solution with 12.8 g (0.015 mole) of 15,19-dihydroxy-13,21-bis(3-chloro-2-hydroxypropyl)-17-dodecyl-13,17,21-triazatriacontane obtained in Synthesis Example 1 dissolved in 30 g of ethanol was added dropwise over 30 minutes. The resultant mixture was aged further for 7 hours. Thereafter, ethanol and unreacted dodecylamine were distilled off under reduced pressure. A mixture of 500 ml of xylene and 500 ml of 5% aqueous sodium hydroxide was added to the residue to subject it to extraction and washing. A xylene layer was taken out and concentrated, thereby obtaining 11.4 g (yield: 61%) of 15,19,23,27-tetrahydroxy-17,21,25-tridodecyl-13, 29-di(hydroxyethyl)-13,17,21,25,29-pentaazahentetracontane represented by the following formula.

Example 7

Preparation of disodium 6,10-dihydroxy-3,13-dioxo-4,8,12-trioctyl-4,8,12-triaza-1,15-pentadecanedicarboxylate A reactor was charged with 17.5 g (0.035 mole) of 11,15-dihydroxy-13-octyl-9,13,17-triazapentacosane and 7.6 g (0.07 mole) of succinic anhydride, to which 100 ml of diethyl ether was added dropwise over 30 minutes. The resultant mixture was stirred for 4 hours at its reflux temperature. Thereafter, water was added to the reaction mixture, and the resulting mixture was washed with water until the pH of a water layer became neutral. Sodium sulfite was added to an ether layer to dewater the ether layer. After filtering the ether layer, the ether was distilled out of the ether layer under reduced pressure. An aqueous solution of sodium hydroxide was added to the residue to dissolve the residue therein. The solution was adjusted to pH 7 and lyophilized, thereby obtaining 34 g (isolation yield: 96%) of disodium 6,10-dihydroxy-3,13-dioxo-4,8,12-trioctyl-4,8, 12-triaza-1,15-pentadecanedicarboxylate.

An ¹H-NMR (solvent: D₂O) chart of this compound is illustrated in FIG. 1.

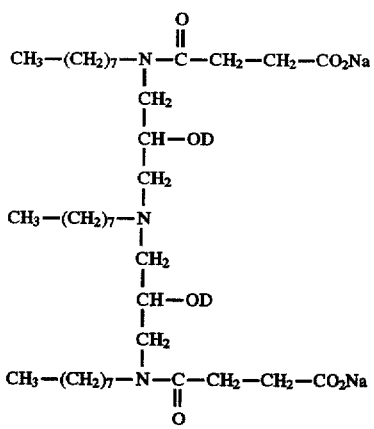

This compound was low in irritativeness and excellent in foamability and gave a pleasant feeling to the user's skin and hair.

Example 8
Preparation of 6-butyl-4,8-dihydroxy-2,10-dioctyl-2,6,10-triaza-1,11-undecanedicarboxylic acid A reactor was charged with 18.6 g (0.04 mole) of 13-butyl-11,15-dihydroxy-9,13,17-triazapentacosane, 100 g of ethanol and 50 g of water, and the contents were heated to 70° C. Thereafter, an aqueous solution of 43 g (0.37 mole) of sodium chloroacetate was added to the contents. The resultant mixture was kept at pH 9 and stirred for 20 hours. After completion of the reaction, ethanol was distilled off under reduced pressure, and the residue was diluted to 10% with water. The resulting solution was adjusted to pH 7, desalted by electrodialysis and lyophilized, thereby obtaining 20.2 g (isolation yield: 85%) of 6-butyl-4,8-dihydroxy-2,10-dioctyl-2,6,10-triaza-1,11-undecanedicarboxylic acid.

The $^1$H-NMR data of this compound will be shown below.

$^1$H-NMR (D$_2$O, δ ppm): 0.85 (triplet,9H,(a)), 1.27 (broad singlet,22H,(b)), 1.60 (broad singlet,6H,(c)), 2.80–3.20 (complicated multiplet, 14H,(d)), 3.51 (complicated multiplet,2H,(e)), 4.00 (broad singlet,4H,(f)).

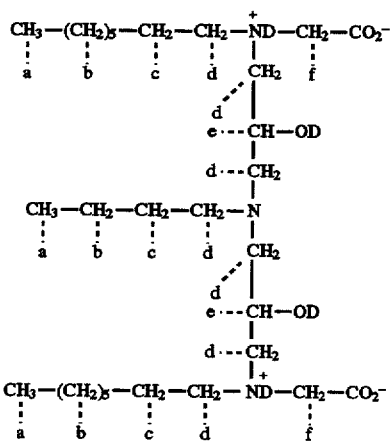

This compound was low in irritativeness and excellent in foamability and gave a pleasant feeling to the user's skin and hair.

Example 9
Preparation of sodium 1,15-dicarboxy-6,10-dihydroxy-3,13-dioxo-4,8,12-trioctyl-4,8,12-triaza-1,15-pentadecanedisulfonate A solution with 3.2 g (0.032 mole) of maleic anhydride dissolved in chloroform was added dropwise over 1 hour to 8 g (0.016 mole) of 11,15-dihydroxy-13-octyl-9,13,17-triazapentacosane in a reactor. The resultant mixture was heated to 50° C. and stirred for 6 hours. Thereafter, the solvent was distilled off under reduced pressure, and a solution with 6.0 g (0.048 mole) of sodium sulfite dissolved in 150 ml of water was added to the residue to react them at 60° C. for 7 hours. After completion of the reaction, the reaction mixture was added with 100 ml of additional water and adjusted to pH 7. The thus-adjusted reaction mixture was then desalted by electrodialysis and lyophilized, thereby obtaining 10.6 g (isolation yield: 71%) of sodium 1,15-dicarboxy-6,10-dihydroxy-3,13-dioxo-4,8,12-trioctyl-4,8,12-triaza-1,15-pentadecanedisulfonate.

The $^1$H-NMR data of the compound treated with 1N HCl will be shown below.

$^1$H-NMR (CDCl$_3$, δ ppm): 0.88 (triplet,9H,(a)), 1.26 (broad singlet,30H,(b)), 1.58 (broad singlet,6H,(c)), 2.65–3.15 (complicated multiplet,10H,(e)), 3.20–3.84 (complicated multiplet,12H,(d)).

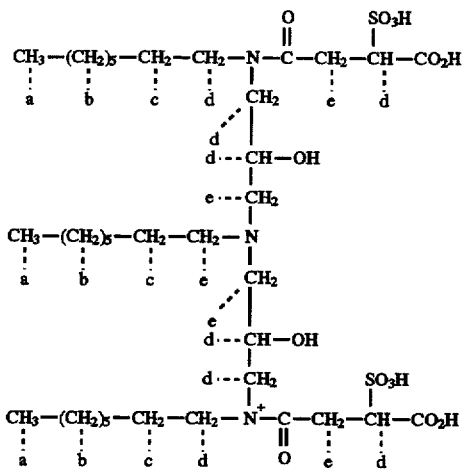

This compound was low in irritativeness and excellent in foamability and gave a pleasant feeling to the user's skin and hair.

Example 10
Preparation of sodium 3,7,11-tridodecyl-3,7,11-triaza-1,5,9,13-tridecanetetrasulfate A reactor was charged with 22.7 g (0.03 mole) of 3,7,11-tridodecyl-3,7,11-triaza-1,5,9,13-tridecanetetraol and 150 ml of dichloromethane, to which 8.8 ml (0.13 mole) of chlorosulfonic acid was added dropwise in a nitrogen stream while chilling with ice water. Thereafter, the temperature of the resulting mixture was gradually raised to room temperature, and hydrochloric acid and dichloromethane generated were purged with a nitrogen stream. Water was added to the residue to dissolve the residue therein, and the solution was adjusted to pH 7.0 with 1N aqueous sodium hydroxide. Thereafter, the solution was desalted by means of a demineralizer (Microacylizer G3, manufactured by Asahi Chemical Industry Co., Ltd.), and then dried by means of a lyophilizer, thereby obtaining 28.1 g (yield: 85.5%) of the title compound.

It was confirmed by thin-layer chromatography (developing solvent: chloroform/methanol=1/1) that this compound showed a single spot (Rf=0.2). Further, the IR spectrum of this compound was as follows:

IR (KBr briquette method, cm$^{-1}$): 1388, 1190 ($v_{S=O}$).

This compound was low in irritativeness and excellent in foamability and gave a pleasant feeling to the user's skin and hair.

Example 11

Preparation of sodium 3,7,11,15,19-pentadodecyl-3,7,11,15, 19-pentaaza-1,5,9,13,17,21-heneicosanehexasulfate A reactor was charged with 12.4 g (0.01 mole) of 3,7,11, 15,19-pentadodecyl-3,7,11,15,19-pentaaza-1,5,9,13,17-21-heneicosanehexaol and 150 ml of dichloromethane, to which 4.4 ml (0.07 mole) of chlorosulfonic acid was added dropwise in a nitrogen stream while chilling with ice water. Thereafter, the temperature of the resulting mixture was gradually raised to room temperature, and hydrochloric acid and dichloromethane generated were purged with a nitrogen stream. Water was added to the residue to disperse the residue therein, and the dispersion was adjusted to pH 7.0 with 1N aqueous sodium hydroxide. Thereafter, the dispersion was desalted by means of a demineralizer (Microacylizer G3, manufactured by Asahi Chemical Industry Co., Ltd.), and then dried by means of a lyophilizer, thereby obtaining 17.0 g (yield: 97%) of the title compound.

It was confirmed by thin-layer chromatography (developing solvent: chloroform/methanol=1/1) that this compound showed a single spot (Rf=0.2). Further, the IR spectrum of this compound was as follows:

IR (KBr briquette method, $cm^{-1}$): 1390, 1182 ($v_{S=O}$).

This compound was low in irritativeness and excellent in foamability and gave a pleasant feeling to the user's skin and hair.

Example 12

Preparation of 6-butyl-4,8-dihydroxy-2,10-dioctyl-2,6,10-triaza-1,1,11,11-undecanetetracarboxylic acid A reactor was charged with 18.6 g (0.04 mole) of 13-butyl-11,15-dihydroxy-9,13,17-triazapentacosane, 100 g of isopropanol and 50 g of water, and the contents were heated to 70° C. Thereafter, an aqueous solution of 43 g (0.37 mole) of sodium chloroacetate was added to the contents. The resultant mixture was kept at pH 9 and stirred for 30 hours under reflux. After completion of the reaction, the solvent was distilled off under reduced pressure, and the residue was dissolved in chloroform to remove unreacted sodium monochloroacetate and salts such as sodium chloride secondarily produced. Thereafter, the product was purified by chromatography on silica gel until a single spot was shown, thereby obtaining 20.2 g of 6-butyl-4,8-dihydroxy-2,10-dioctyl-2,6,10-triaza-1,1,11,11-undecanetetracarboxylic acid.

The $^1$H-NMR data of this compound will be shown below.

$^1$H-NMR (D$_2$O, δ ppm): 0.85 (triplet,9H,(a)), 1.27 (broad singlet,22H,(b)), 1.60 (broad singlet,6H,(c)), 3.05–3.30 (complicated multiplet,14H,(d)), 3.55 (complicated multiplet,2H,(e)), 4.10 (broad singlet,4H,(f)).

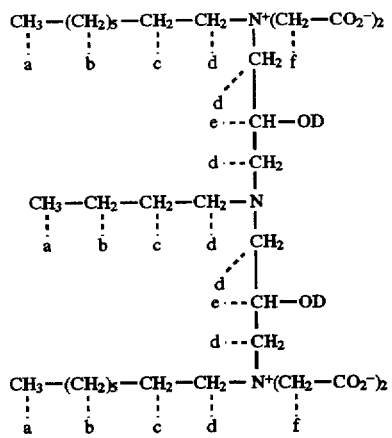

This compound was low in irritativeness and excellent in foamability and gave a pleasant feeling to the user's skin and hair.

Test Example 1

The cytotoxic effect of the compounds according to the present invention was tested in accordance with the following method.

(Testing method)

Four days prior to exposure to a substance to be tested, SIRC cells (established cell line of fibroblasts in the epithelial parenchymal layer of a rabbit eye) were disseminated on a 96-well plate in a concentration of $3 \times 10^3$ cells/well to culture them under conditions of 37° C. and 5% $CO_2$.

The test substance was dissolved in physiological saline to give a concentration of 1 wt. % or 10 wt. %. This solution was diluted with a culture medium. After the thus-obtained test solution was added to the culture solution to conduct culture for 48 hours, the culture solution was washed twice with PBS (pH 7.4) and fixed in methanol to stain with a Giemsa stain. After washing and drying, a mixture of 1N HCl/ethanol (1/9) was added to extract the stained solution, followed by measurement by means of a microplate reader (655 nm). The concentration at which 50% of the test solutions were stained was expressed as IC$_{50}$(ppm).

(Result)

As shown in Table 1, the test revealed that the compounds according to the present invention were weak in cytotoxic effect and hence high in safety.

TABLE 1

| Compound tested | IC$_{50}$ (ppm) |
|---|---|
| Sodium dodecyl sulfate | 82 |
| Compound of Example 10 | 790 |
| Compound of Example 11 | 1000< |

Formulation Example 1

A shampoo having the following composition was prepared using the compound according to the present invention.

| (Composition) | (wt. %) |
| --- | --- |
| Compound of Example 7 | 15.0 |
| Lauroyldiethanolamide | 3.0 |
| Lauryldimethylamine oxide | 0.5 |
| Hydroxyethylcellulose (product of Daicel Chemical Industries, Ltd.) | 0.1 |
| Sodium benzoate | 0.3 |
| Coloring matter | Proper amount |
| Perfume base | Proper amount |
| Citric acid | Proper amount |
| Water | Balance |
| Total | 100.0 |

Formulation Example 2

Shampoos were prepared in the same manner as in Formulation Example 1 except that the compounds of Examples 8–11 were separately used instead of the compound of Example 7.

All the shampoos obtained in Formulation Examples 1 and 2 were excellent in foamability and detergency, and good even in a feel upon shampooing and rinsing.

Formulation Example 3

A body shampoo having the following composition was prepared using the compound according to the present invention.

| (Composition) | (wt. %) |
| --- | --- |
| Compound of Example 8 | 17.0 |
| Polyoxyethylene (EO 3) laurylglucoside | 5.0 |
| Lauryldimethylamine oxide | 3.0 |
| Glycerin | 4.0 |
| Sucrose fatty acid ester | 1.0 |
| Methylparaben | 0.3 |
| Coloring matter | Proper amount |
| Perfume base | Proper amount |
| Citric acid | Proper amount |
| Water | Balance |
| Total | 100.0 |

Formulation Example 4

Body shampoos were prepared in the same manner as in Formulation Example 3 except that the compounds of Examples 7, and 9 to 11 were separately used instead of the compound of Example 8.

All the body shampoos obtained in Formulation Examples 3 and 4 were excellent in foamability and detergency, and good even in a feeling after washing because they gave a moisturized feeling.

Formulation Example 5

A face cleanser having the following composition was prepared using the compound according to the present invention.

| (Composition) | (wt. %) |
| --- | --- |
| Potassium laurate | 4.0 |
| Potassium myristate | 4.0 |
| Compound of Example 9 | 10.0 |
| Glycerin | 15.0 |
| Ethylene glycol distearate | 2.0 |
| Cationic cellulose | 0.2 |
| Water | Balance |
| Total | 100.0 |

Formulation Example 6

A face cleanser having the following composition was prepared using the compound according to the present invention.

| (Composition) | (wt. %) |
| --- | --- |
| Compound of Example 10 | 8.0 |
| Potassium monolauryl phosphate | 6.0 |
| Potassium laurate | 2.0 |
| Potassium myristate | 2.0 |
| Potassium stearate | 2.0 |
| Stearic acid | 4.0 |
| Octylglycoside | 3.0 |
| 1,3-Butylene glycol | 10.0 |
| Perfume base | Trace amount |
| Water | Balance |
| Total | 100.0 |

Test Example 2

A dishwashing detergent having the following composition was prepared to evaluate it in foaming power, detergency, iritativeness to the skin and a feel upon use (feeling of touch to the hands).

| (Composition) | (wt. %) |
| --- | --- |
| Compound of Example 10 | 5.0 |
| Sodium polyoxyethylene (average number of moles added: 3) lauryl ether sulfate | 12.0 |
| Lauryldimethylamine oxide | 3.0 |
| Coconut oil fatty acid monoethanolamide | 5.0 |
| Ethanol | 2.5 |
| Sodium m-xylenesulfonate | 2.0 |
| Sodium benzoate | 1.0 |
| Coloring matter | Proper amount |
| Perfume base | Proper amount |
| Water | Balance |
| Total | 100.0 |

<Testing method>

Beef tallow added with 0.1 wt. % of Sudan III (a red coloring matter) as an indicator was applied in an amount of 2.5 g to a porcelain dish (diameter: 25 cm). The thus-smeared dish was rubbed and washed at 40° C. by means of a sponge with 3 g of the detergent sample and 27 g of water (hardness: 3.5°DH) soaked therein. The above-described test was conducted on ten panelists to evaluate the detergent sample in the detergency, feel upon use, etc.

<Results>

As a result, the dishwashing detergent in which the compound according to the present invention was incorporated was good in foaming power, high in detergency and low in irritativeness to the hands and gave users a pleasant feel upon use.

Formulation Example 7

A powdery laundry detergent composition having the following composition was prepared. This detergent composition was excellent in detergency at a low temperature (5° C.), and its detergency was not impaired even when water high in hardness (4°–8°DH) was used.

| (Composition) | (wt. %) |
|---|---|
| Compound of Example 8, 10 or 11 | 5.0 |
| Polyoxyethylene (EO 4–18) $C_6$—$C_{22}$ alkyl ether | 3.0 |
| Sodium $C_{12}$-alkylbenzenesulfonate | 20.0 |
| Sodium $C_{12}$–$C_{14}$-alkylsulfate | 5.0 |
| Sodium salt of $C_{12}$—$C_{18}$ fatty acid | 6.0 |
| Zeolite (4A type) | 30.0 |
| Sodium carbonate | 20.0 |
| Enzyme (protease, cellulase) | 2.0 |
| Polymer (acrylic acid-maleic acid copolymer, Mw = 50,000) | 3.0 |
| Fluorescent dye (DM type, Tinopal CBS mixed system) | 0.5 |
| Perfume base | 0.2 |
| Water | Balance |
| Total | 100.0 |

Formulation Example 8

A powdery laundry detergent composition having the following composition was prepared. This detergent composition was excellent in an effect of finishing washed clothes softly and with good hand and feel.

| (Composition) | (wt. %) |
|---|---|
| Compound of Example 7 | 10.0 |
| Polyoxyethylene (EO 4–18) $C_6$—$C_{22}$-alkyl ether | 25.0 |
| Cationic cellulose | 3.0 |
| Sodium salt of $C_{12}$–$C_{18}$ fatty acid | 6.0 |
| Zeolite (4A type) | 20.0 |
| Sodium carbonate | 20.0 |
| Amorphous aluminosilicate ($Na_2O.Al_2O_3.3\ SiO_2$) | 10.0 |
| Enzyme (protease, cellulase) | 2.0 |
| Polymer (sodium polyacrylic acid, Mw = 50,000) | 3.0 |
| Fluorescent dye (DM type, Tinopal CBS mixed system) | 0.5 |
| Perfume base | 0.2 |
| Water | Balance |
| Total | 100.0 |

Formulation Example 9

A powdery laundry detergent having the following composition and composed principally of a nonionic surfactant was prepared. According to this detergent, the disadvantages that foaming upon washing is little and rinsability is poor, which are problems involved in the conventional detergents composed principally of a nonionic surfactant, were improved.

| (Composition) | (wt. %) |
|---|---|
| Compound of Example 8 | 5.0 |
| Polyoxyethylene (EO 4–18) $C_6$—$C_{22}$-alkyl ether | 22.0 |
| Sodium salt of $C_{12}$–$C_{18}$ fatty acid | 1.0 |

-continued

| (Composition) | (wt. %) |
|---|---|
| Zeolite (4A type) | 30.0 |
| Sodium carbonate | 25.0 |
| Amorphous aluminosilicate ($Na_2O.Al_2O_3.3\ SiO_2$) | 10.0 |
| Enzyme (protease, cellulase) | 2.0 |
| Polymer (acrylic acid-maleic acid copolymer, Mw = 100,000) | 3.0 |
| Fluorescent dye (DM type, Tinopal CBS mixed system) | 0.5 |
| Perfume base | 0.2 |
| Water | Balance |
| Total | 100.0 |

INDUSTRIAL APPLICABILITY

The amine derivatives, or salts or quaternized products thereof, which are novel compounds according to the present invention, are excellent in foamability and low in irritativeness to the skin and the like, and can give a pleasant feeling to the user's skin, hair and the like. Therefore, the compounds according to the present invention are useful as bases for hair and skin cosmetic compositions, detergents, emulsifying agents, wetting agents, conditioning agents, or the like.

We claim:

1. An amine represented by the following general formula (1):

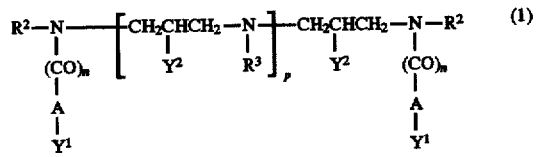

wherein $R^2$ and $R^3$ are identical with or different from each other and mean individually a linear or branched alkyl or alkenyl group which may be substituted by a hydroxyl group and has 1–24 carbon atoms, A denotes a linear or branched alkylene or alkenylene group which may be substituted by at least one hydroxyl, carboxyl or sulfonic group and has 1–6 carbon atoms, $Y^1$ is a carboxyl or sulfonic group, or a sulfuric acid residue, $Y^2$ means a hydroxyl group, a sulfuric acid residue or a group —OCO—A—COOH, n stands for a number of 0 or 1, and p is an integer of 1–8, or a salt or quaternized product thereof.

2. The compound according to claim 1, wherein $Y^1$ is a sulfonic group or a sulfuric acid residue, and $Y^2$ is a hydroxyl group or a sulfuric acid residue.

3. The compound according to claim 1, wherein $Y^1$ is a carboxyl group, and $Y^2$ is a hydroxyl group or a group —OCO—A—COOH.

4. The compound according to claim 1, wherein $R^2$ and $R^3$ are individually a linear or branched alkyl or alkenyl group having 6–24 carbon atoms.

5. The compound according to claim 1 which is in the form of a free base or a salt.

6. A detergent composition comprising the compound according to claim 1 and a detergent base.

* * * * *